US008999427B2

(12) United States Patent
Ruppel

(10) Patent No.: US 8,999,427 B2
(45) Date of Patent: Apr. 7, 2015

(54) PROCESS AND APPARATUS FOR IMPREGNATING A PRODUCT OBTAINED BY CUTTING A CONTINUOUS WEB

(75) Inventor: Remy Ruppel, Durrenentzen (FR)

(73) Assignee: SCA Tissue France, Saint-Ouen (FR)

( * ) Notice: Subject to any disclaimer, the term of this patent is extended or adjusted under 35 U.S.C. 154(b) by 1273 days.

(21) Appl. No.: 12/030,238

(22) Filed: Feb. 13, 2008

(65) Prior Publication Data
US 2008/0195069 A1 Aug. 14, 2008

(30) Foreign Application Priority Data
Feb. 13, 2007 (FR) ...................................... 07 01035

(51) Int. Cl.
*A61L 33/00* (2006.01)
*A61F 13/15* (2006.01)

(52) U.S. Cl.
CPC ................. *A61F 13/15723* (2013.01)

(58) Field of Classification Search
USPC ............... 117/140; 128/190; 101/401.1, 353; 91/14; 154/37; 229/55; 206/41.2
See application file for complete search history.

(56) References Cited

U.S. PATENT DOCUMENTS

| 1,555,238 | A | | 9/1925 | Chambon | |
|---|---|---|---|---|---|
| 1,949,419 | A | * | 3/1934 | Johnson | 156/555 |
| 2,216,594 | A | * | 10/1940 | Marchev | 427/144 |
| 2,263,158 | A | * | 11/1941 | Benton | 118/37 |
| 2,275,063 | A | * | 3/1942 | Arlington | 383/108 |
| 3,004,868 | A | * | 10/1961 | Sumner et al. | 442/104 |
| 3,183,910 | A | * | 5/1965 | Patterson | 604/381 |
| 3,333,683 | A | * | 8/1967 | Scharre | 206/245 |

FOREIGN PATENT DOCUMENTS

WO 9727032 A1 7/1997

OTHER PUBLICATIONS

Search report, FR 0701035 dated Jan. 2, 2008.

* cited by examiner

*Primary Examiner* — Dah-Wei D Yuan
*Assistant Examiner* — Andrew Bowman
(74) *Attorney, Agent, or Firm* — Drinker Biddle & Reath LLP

(57) ABSTRACT

The invention relates to a method for the impregnation of a product consisting of fibrous material and formed from a continuous web (22), the method comprising at least one first step of cutting out a specific zone (24) of the continuous web (22) and at least one second step of applying an impregnation product to the specific zone (24), the first and second steps being carried out simultaneously or virtually simultaneously.

7 Claims, 3 Drawing Sheets

PROCESS AND APPARATUS FOR IMPREGNATING A PRODUCT OBTAINED BY CUTTING A CONTINUOUS WEB

This application claims priority to copending French patent application number 07 01035, filed Feb. 13, 2007, the disclosure of which is incorporated herein by reference.

The invention relates to a novel method and a novel device for the impregnation of a product produced by cutting out a continuous web of fibrous material.

In the field of products consisting of fibrous materials, it is often expedient to cut out a series of individual formats within a continuous web.

To be precise, cutting out a web continuously makes it possible to increase the production outputs, the speed of execution being much higher than that in cutting out sheet by sheet.

Moreover, this likewise facilitates the process of treating the cut-out products downstream, in particular their packaging or their possible impregnation.

This method generally makes it necessary to employ a specific apparatus adapted to the dimensions and characteristics of the web to be cut out and also to the format of the cut-out products to be obtained.

Furthermore, additional apparatuses are used in order to carry out the other treatment steps, each of the apparatuses acting, according to circumstances, either on the continuous web or on each individual cut-out product.

Where cut-out and impregnated products are concerned, then, it is found that the methods and devices available at the present time in this regard have a certain number of disadvantages which prove incompatible with increased profitability and a high product quality.

A prior art involves, in particular, impregnating the continuous web before the cutting-out step.

The disadvantage of this method is that impregnation takes place homogenously over the entire surface of the web, including in the zones removed from the web once the cutting-out step has been carried out.

This results in a needless consumption of impregnation product.

Another prior art involves individually impregnating each cut-out zone of the web downstream of the cutting-out step.

The disadvantage of this solution is that it is difficult to apply the impregnation product exactly at the location of the cut-out zone.

This often results in an incomplete and random impregnation of the final products.

Another disadvantage of these solutions is the need to provide two separate apparatuses for carrying out the cutting-out and impregnation.

The invention is therefore aimed at proposing a solution to the problem of the impregnation of products produced by cutting out a continuous web, the solution not having the disadvantages of the abovementioned prior art.

To achieve this, and according to the invention, a method for the impregnation of a product consisting of fibrous material and formed from a continuous web is proposed, the method comprising at least one first step of cutting out a specific zone of the continuous web and at least one second step of applying an impregnation product to the specific zone, the method being notable in that the first and second steps are carried out simultaneously or virtually simultaneously.

In an advantageous variant of the method of the invention, the first and second steps are carried out at least partially by means of one and the same apparatus.

In another variant of the method of the invention, the continuous web is formed from a non-woven material, in particular a cotton web.

In another variant of the method of the invention, the continuous web is formed from a cellulose material, in particular a paper sheet.

In another variant of the method of the invention, the impregnation product is a liquid.

In another variant of the method of the invention, the impregnation product is a paste.

In another variant of the method of the invention, the product obtained is a cotton make-up removing pad or a wet wipe.

In another variant of the method of the invention, the product obtained is a sanitary towel or a baby's napkin or an adult's napkin.

The invention also relates to a device intended for carrying out the abovementioned method, the device being notable in that it comprises at least one first means for cutting out a specific zone of a continuous web formed from a fibrous material and at least one second means for applying an impregnation product to the specific zone, the first and second means being in one piece.

In an advantageous variant of the device of the invention, the second means is arranged in relation to the first means so as to be in contact with or opposite to the specific zone at the moment of the cut-out.

In another variant of the device of the invention, the first means consists of a roller provided with a recess or relief pattern, the edges of which are cutting and substantially delimit the specific zone to be cut out, the continuous web being pressed between this roller and a smooth roller, called an anvil roller, so as to carry out the cut-out.

In another variant of the device of the invention, the first means consists of a blade mounted on a support.

In another variant of the device of the invention, the blade is movable in the support.

In another variant of the device of the invention, the support is curved and is preferably cylindrical.

In another variant of the device of the invention, the support is plane.

In another variant of the device of the invention, the first means is a punch, the continuous web being pressed between this punch and a die pierced with at least one hole, the dimensions of which correspond to those of the specific zone to be cut out, so as to carry out the cut-out.

In another variant of the device of the invention, the second means comprises a nozzle capable of projecting the impregnation product in the direction of the continuous web.

In another variant of the device of the invention, the second means comprises an absorbent body capable of containing a certain quantity of impregnation product and of transferring at least part of the product onto the web when it is pressed against the latter.

In another variant of the device of the invention, the second means comprises a non-absorbent body capable of retaining a certain quantity of impregnation product on its surface and of transferring at least part of the product onto the web when it is put into contact with the latter.

As configured, therefore, the invention will make it possible to deposit the impregnation product solely on the cut-out zones of the continuous web, thus avoiding the needless overconsumption of product.

Furthermore, since cutting-out and impregnation take place during a common treatment step and/or using a single apparatus, this will result in a saving of time and of space which is advantageous for the productivity and overall efficiency of the method for manufacturing the final products.

Other advantages and characteristics will become more clearly apparent from the following description of a method and a device according to the invention, with reference to the drawings in which.

Figure 1:
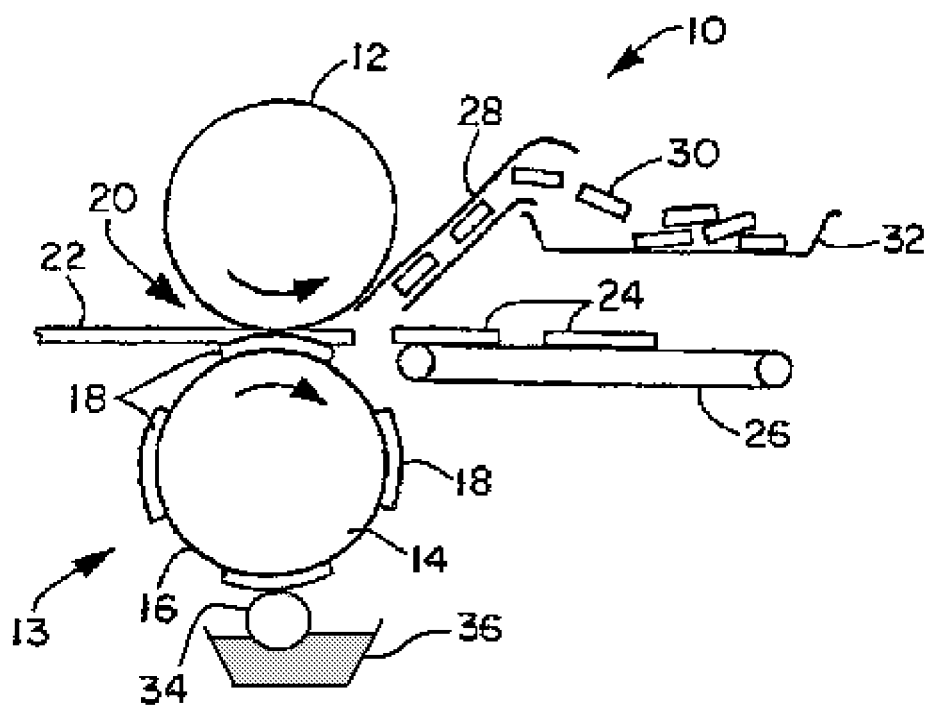
FIG. 1 illustrates a diagrammatic view of an impregnation device according to the invention.

Referring to FIG. 1, this illustrates a rotary cutting-out apparatus 10 comprising an anvil roller 12 cooperating with a cutting-out roller 13. The anvil roller 12 may be formed from a ferric or non-ferric metal and possess a smooth surface. The anvil roller 12 may likewise be formed from a compressible material, such as neoprene.

Even if, in the figure illustrated, the anvil roller 12 is arranged above the cutting-out roller 13, it will nevertheless be preferable to arrange the cutting-out roller 13 above the anvil roller 12, so as to assist the transfer of the impregnation product by gravity.

The cutting-out roller 13 comprises a cylindrical support 14 provided with an outer circumference 16 and at least one cutting-out insert 18 mounted on the cylindrical support 14.

The insert 18 can be fastened to the support 14 by means of a bolt so as to make it possible to replace it quickly during the phases of cleaning or of changing the cutting-out format.

The cutting-out roller 13 will advantageously be formed from a rigid metal, for example from steel, so as to prevent the deformations of its outer surface during its use.

The cutting-out roller 13 can advantageously possess a plurality of cutting-out inserts 18 distributed uniformly on the circumference 16 of the support 14, the inserts 18 preferably describing a circle about the axis of the support 14 and being spaced at a constant angle.

In the example illustrated in FIG. 1, the cutting-out roller 13 comprises four inserts 18 spaced equally on the outer circumference 16 of the support 14, the inserts 18 being arranged in a circle about the axis of the support 14.

The cutting-out roller 13 and the anvil roller 12 execute a rotation in opposite directions and cooperate to form a nipping zone 20, through which passes a web 22 of fibrous material of the non-woven type, such as, for example, a cotton web, or of the cellulose type, such as, for example, a paper sheet.

At the moment when it passes through the nipping zone 20, the web 22 is pressed between one of the inserts 18 of the cutting-out roller 13 and the smooth surface of the anvil roller 12, thus causing the web 22 to be cut out into individual articles 24. Since cutting-out takes place substantially along the outer edges of the inserts 18, each of the articles 24 obtained therefore has the form of the insert 18 used.

During this cutting-out operation, a deposit of impregnation product onto that face of the article 24 which was in contact with the insert 18 likewise occurs.

This impregnation occurs virtually simultaneously, and preferably simultaneously, with the cutting-out of the article 24. As used herein, the terms "simultaneously" or "virtually simultaneously" means a time less than or equal to one second, specifically 0 seconds to 0.5 seconds.

It may, in particular, arise as a result of the action of a means for applying impregnation product which is integrated in the cutting-out roller 13, the application means advantageously being arranged in a zone covered by the insert or inserts 18.

Thus, when the web 22 passes through the nipping zone 20, that is to say opposite to and/or in contact with that zone of the cutting-out roller 13 which is covered by the insert 18, the web is normally in the zone of action of the application means and is therefore capable of receiving a quantity of impregnation product from the latter.

Once cut-out and impregnated, the articles 24 are transported by conventional means, such as a conveyor belt 26, towards a location where they can be stacked, packaged and subsequently dispatched, for example in the form of pallets.

The web waste 30 remaining after the cutting-out operation can be directed out of the nipping zone 20 towards a duct 28, using a suction or blowing means, gravity or other conventional mechanical means. This waste 30 is then collected in a discharge bin 32, before being recycled or destroyed.

Figure 2A:
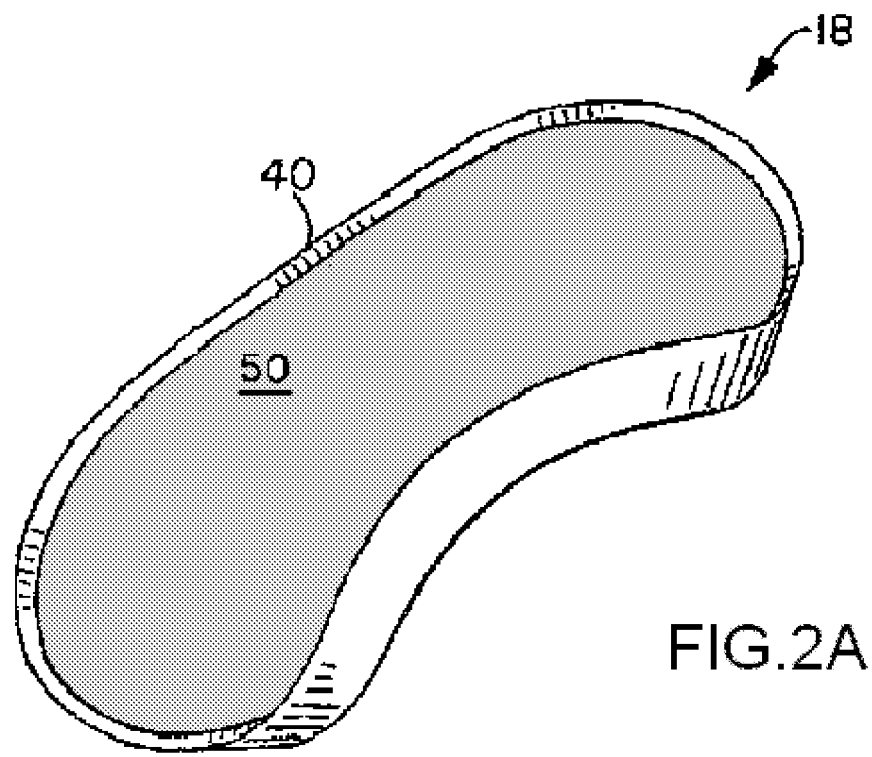
FIGS. 2A, 2B and 2C illustrate perspective views of cutting-out inserts capable of being used in the device illustrated in FIG. 1.
Figure 2B:
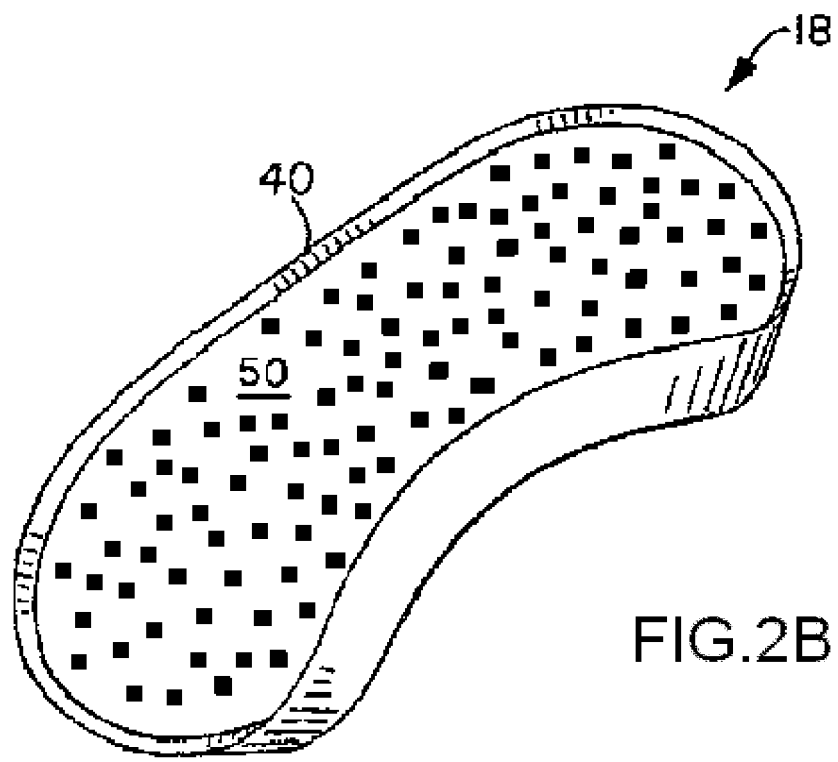
Figure 2C:
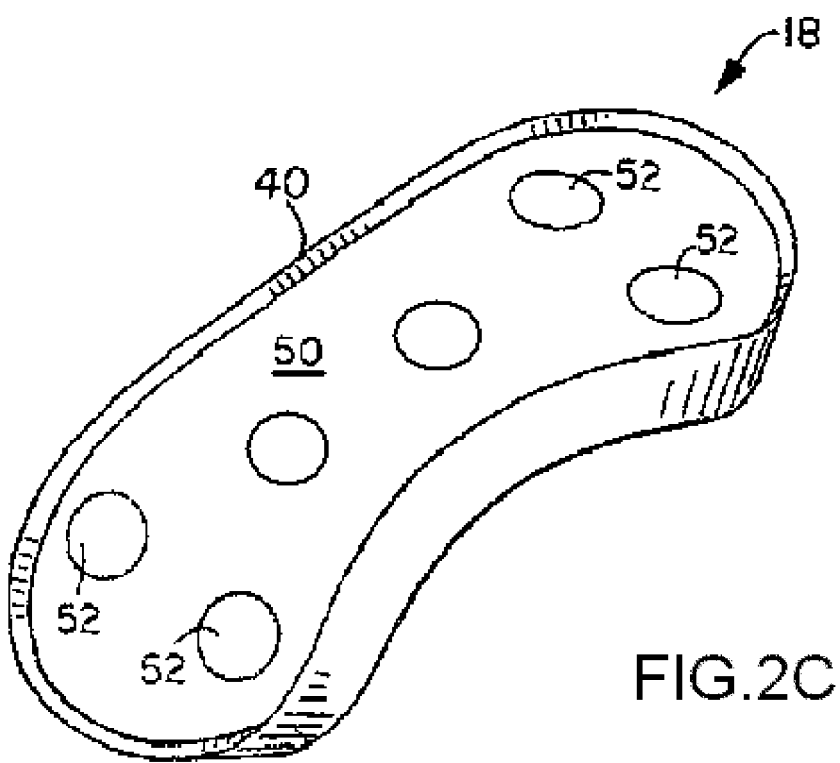

Referring to FIGS. 2A, 2B and 2C, these illustrate examples of inserts which can be used within the framework of the device illustrated in FIG. 1.

These inserts 18 are designed, by virtue of their form, to carry out the cutting-out of sanitary towels. It is clear that the form of the inserts 18 can be adapted as a function of the articles to be formed. In particular, it will be conceivable to use inserts 18 of round, oval, square or rectangular form in order to produce cotton make-up removing pads.

These inserts 18 likewise possess a curvature so as to adapt to the curvature of the cylindrical support 14 on which they must be fastened.

Each of them possess a cutting edge 40 on its periphery, so as to carry out the cutting-out of the continuous web 22 when it presses the latter against the anvil roller 12 in the above-mentioned nipping zone 20. This cutting edge 40 may be continuous, as in the examples illustrated, or discontinuous in order to form pre-cuts. It may likewise comprise a series of teeth over the whole or part of its length.

The cutting edge 40 delimits an inner wall 50 of the insert.

This inner wall 50 will preferably possess a height lower than that of the cutting edge 40, in order to be arranged so as to be set back with respect to the latter.

In the embodiments illustrated in FIGS. 2A, 2B and 2C, furthermore, this inner wall 50 forms means for applying a product, liquid or paste, to the continuous web.

In the example of FIG. 2A, this inner wall 50 is substantially smooth and possesses surface properties making it capable of retaining a liquid or a paste in the form of a more or less fine layer on its surface and of depositing at least part of the liquid or of the paste onto the continuous web 22 when they are put into contact, especially in the nipping zone 20. The liquid or paste will have been deposited onto the inner wall 50 beforehand, especially before the cutting-out step, using any means conventional in this regard. An additional coating roller 34 may, for example, be arranged in the device illustrated in FIG. 1, upstream of the nipping zone 20, and will be configured so as to deposit a layer of liquid or of paste onto the inner wall 50 of the insert 18. This coating roller 34 will advantageously consist of a compressible material so as to be pressed easily against the insert. It will likewise consist of an absorbent material so as to contain a certain quantity of liquid or of paste within it and so subsequently to transfer more or less of this liquid or this paste onto the insert 18 as a function of the pressure which it exerts on the insert 18. The liquid or paste may, in particular, come from a container 36 in which the coating roller 34 will be partially immersed.

It is likewise conceivable to replace this coating roller 34 by a felt strip partially immersed in a liquid or impregnated with a liquid or with a paste and in point contact with the cutting-out roller 13, so as to coat the inserts 18 at least partially with liquid or with paste.

In the example of FIG. 2B, the inner wall 50 is formed from a compressible and absorbent material which may possess characteristics substantially similar to those of the material used for forming the above-mentioned coating roller 34.

The wall 50 will contain within it the liquid or paste intended for impregnating the continuous web 22, the liquid or the paste having been applied beforehand to the wall 50 by any conventional means. It is conceivable, in particular, to cause the inserts 18 of the cutting-out roller 13 of FIG. 1 to pass through a trough filled with the liquid or with the paste, upstream of the nipping zone 20, so as to impregnate with it the inner walls 50 of the inserts 18. There may likewise be provision for installing a reservoir of liquid or of paste inside the cylindrical support 14 of the cutting-out roller 13, the reservoir being in direct or indirect communication with the inner wall 50.

In the example of FIG. 2C, the inner wall 50 is pierced with a series of holes 52, each of the holes 52 being arranged opposite to and in the extension of a liquid or paste ejection nozzle, not illustrated, fastened inside the wall 50 or integrated in the cylindrical support 14 of the cutting-out roller 13.

By synchronizing the liquid or paste injection step with the cutting-out step, in particular by actuating the nozzles at the moment when the holes 52 are opposite the web zone 24 to be cut out, that is to say when the insert 18 is located in the nipping zone 20, it is possible to apply the liquid or paste solely in the zone to be cut out 24 and simultaneously or virtually simultaneously with the cut-out.

Furthermore, there may be provision for feeding the nozzles by means of feed pipes connected to one or more reservoirs inside or outside the cutting-out roller, each of the reservoirs being capable of containing a particular liquid or paste.

In an alternative embodiment, not illustrated, it is conceivable to replace the ejection nozzles by any liquid projection system. In particular, an inner space within the cylindrical support 14 may be provided, in which an internal pressure will be generated so as to extrude the impregnation product through the holes 52 of the inner wall 50. Moreover, the inner zone 50 will advantageously be formed from a compressible and absorbent material, so as to restore the product even to the parts of the continuous web 22 which are not arranged opposite to or in the vicinity of the holes 52, the product quantity applied to these parts nevertheless being smaller than that supplied directly through the holes 52.

The holes 52 may be distributed uniformly over the entire surface of the inner wall 50. However, it would be advantageous to arrange them in the form of concentric circles, the holes 52 of the circles nearest the centre possessing a larger diameter than the holes 52 of the circles nearest the periphery, so as to apply more product in the central part of the cut-out zone 24 than on the edges.

In another alternative embodiment, not illustrated, it will likewise be conceivable to make the cutting edge movable with respect to the cylindrical support.

It will thus be possible to displace this cutting edge from a position of rest, where it will be positioned beneath the outer surface of the above-mentioned inner wall, into an active cutting-out position, where it will project with respect to this same surface.

This displacement may take place at the moment when the inner wall will be opposite the web to be cut out in the nipping zone. It may, in particular, be caused by the action of a cam arranged within the cutting-out roller and eccentric with respect to the axis of the roller, which cam will act on another of the edges of the knife or of the blade carrying the cutting edge.

Figure 3:
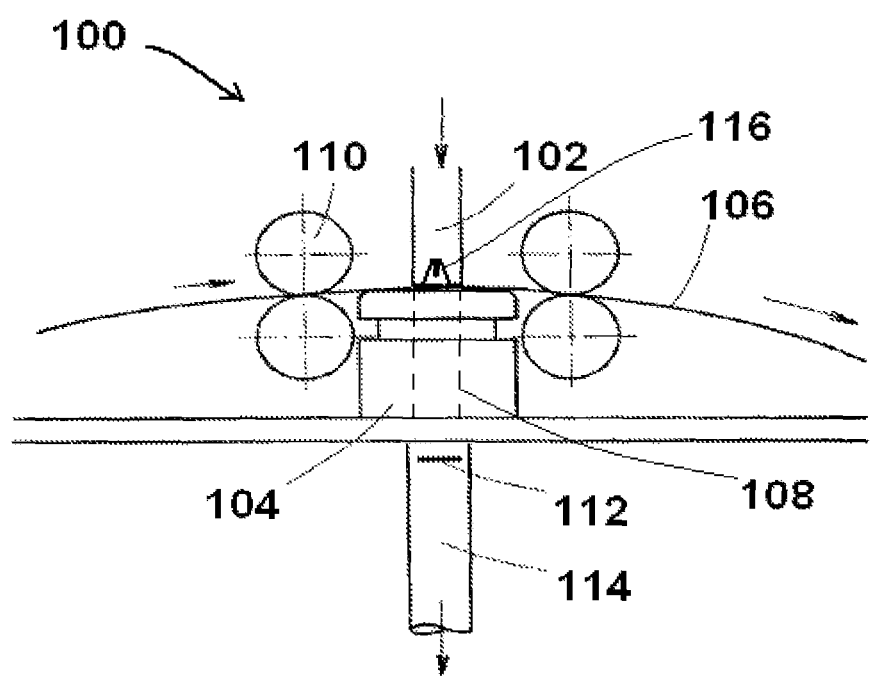
FIG. 3 illustrates diagrammatically an alternative embodiment of an impregnation device according to the invention.

Referring to FIG. 3, this illustrates an alternative embodiment of a cutting-out device according to the invention.

The cutting-out device 100 is composed of a punch 102 cooperating with a die 104, between which a web 106 of fibrous material travels, which is driven in a stepping movement at a particular frequency.

The die 104 comprises a central aperture 108 capable of receiving the punch 102, the form of the aperture 108 defining the cutting-out pattern.

In order to adjust the position of the web 106 with respect to the die 104 and to the punch 102, it is passed between drive rollers 110 before and after the cutting-out.

At a given frequency corresponding substantially to that of the movement of the web 106, the punch 102 is displaced abruptly through the aperture 108 of the die 104, so as to cause the web 106 to be cut out.

A wafer 112 of material possessing the form of the aperture 108 then falls, under the effect of its weight, into a tubular member 114 arranged beneath the die 104 and is subsequently collected in a bag, not illustrated, placed under the tubular member 114.

To allow the simultaneous impregnation of the cut-out wafers 112, the punch 102 is equipped with one or more ejection nozzles 116 arranged in the punch 102 and communicating with that face of the punch 102 which is intended for striking the web 106, the nozzle or nozzles 116 being fed with impregnation product from an inner or outer reservoir and using conventional means.

In another variant of the invention, it is likewise conceivable to use, as a means for applying the impregnation product, that surface of the punch 102 which is intended for striking the web 106. This surface will therefore possess surface properties making it capable of retaining the product until the latter is transferred onto the web 106 by contact. Any conventional means may be used, moreover, in order to deposit the product onto the surface before the cutting-out step.

It goes without saying that the exemplary embodiments given above are in no way limiting with regard to the present invention, other modifications or additions in the steps of the method or in the means implemented with regard to the device being conceivable without departing from the scope of the invention.

Moreover, the articles obtained by means of the impregnation method of the present invention may, depending on circumstances, be either dry or wet, as a function of the product quantity applied.

What is claimed is:

1. A method for impregnation of a product comprising fibrous material and formed from a continuous web, the method comprising:
    cutting out and removing a specific zone from the continuous web of fibrous material using a cutting element having a cutting edge forming a periphery of an inner wall of the cutting element, the inner wall having a shape substantially corresponding to the specific zone; and
    applying an impregnation product to the specific zone, wherein the cutting out and removing step and the applying step are carried out simultaneously or virtually simultaneously and wherein the cutting edge cuts out the specific zone and the impregnation product is applied by the inner wall of the cutting element.

2. The method according to claim 1, wherein the continuous web is formed from a non-woven material.

3. The method according to claim 1, wherein the continuous web is formed from a cellulose material.

4. The method according to claim 1, wherein the impregnation product is a liquid.

5. The method according to claim 1, wherein the impregnation product is a paste.

6. The method according to claim 1, wherein the cutting element is a roller provided with a recess or relief pattern defined by the inner wall, and the cutting edge substantially delimits the specific zone to be cut out, the continuous web being pressed between this roller and a smooth roller.

7. The method according to claim 1, wherein the cutting element is a punch, the continuous web being pressed between this punch and a die pierced with at least one hole, the dimensions of which correspond to those of the specific zone to be cut out.

* * * * *